(12) United States Patent
Kawamura et al.

(10) Patent No.: US 9,308,328 B2
(45) Date of Patent: Apr. 12, 2016

(54) PLUNGER ROD AND SYRINGE

(75) Inventors: Hideaki Kawamura, Tokyo (JP);
Hiroshi Togashi, Tokyo (JP)

(73) Assignee: DAIKYO SEIKO, LTD, Tokyo (JP)

( * ) Notice: Subject to any disclaimer, the term of this patent is extended or adjusted under 35 U.S.C. 154(b) by 568 days.

(21) Appl. No.: 12/866,699

(22) PCT Filed: Feb. 29, 2008

(86) PCT No.: PCT/JP2008/053603
§ 371 (c)(1),
(2), (4) Date: Aug. 6, 2010

(87) PCT Pub. No.: WO2009/107224
PCT Pub. Date: Sep. 3, 2009

(65) Prior Publication Data
US 2010/0318036 A1    Dec. 16, 2010

(51) Int. Cl.
*A61M 5/315* (2006.01)
*A61M 5/31* (2006.01)

(52) U.S. Cl.
CPC ... *A61M 5/31511* (2013.01); *A61M 2005/3121* (2013.01); *A61M 2205/583* (2013.01); *A61M 2205/6081* (2013.01)

(58) Field of Classification Search
CPC .................................................. A61M 5/31511
USPC .................... 604/181, 187, 189, 218, 68, 227
See application file for complete search history.

(56) References Cited

U.S. PATENT DOCUMENTS

| | | | | |
|---|---|---|---|---|
| 3,921,633 | A | * | 11/1975 | Tischlinger .................... 604/227 |
| 6,096,005 | A | * | 8/2000 | Botich et al. ................... 604/110 |
| 6,572,584 | B1 | * | 6/2003 | Shaw et al. .................... 604/110 |
| 6,918,889 | B1 | | 7/2005 | Brunel |
| 2004/0186437 | A1 | * | 9/2004 | Frenette et al. ............... 604/189 |
| 2006/0084919 | A1 | * | 4/2006 | Shaw et al. ................... 604/110 |
| 2008/0021389 | A1 | * | 1/2008 | Runfola .............. A61M 5/3234 604/110 |

FOREIGN PATENT DOCUMENTS

| | | |
|---|---|---|
| JP | 359072 Z2 | 11/1956 |
| JP | 2003-501218 A | 1/2003 |
| JP | 2003-260136 A | 9/2003 |

(Continued)

OTHER PUBLICATIONS

International Search Report for PCT/JP2008/053603 dated Mar. 25, 2008.

(Continued)

*Primary Examiner* — Kevin C Sirmons
*Assistant Examiner* — Shefali Patel
(74) *Attorney, Agent, or Firm* — Kenealy Vaidya LLP

(57) ABSTRACT

Disclosed is a plunger rod for a syringe. The plunger rod is useful for sliding a piston within a syringe barrel. The plunger rod is characterized in that it is colored in part or in whole. The syringe is also disclosed. According to such plunger rods, even plural syringes of exactly the same external appearance and configuration can be applied with features that make it possible to readily and visually identify them by simply taking a glance at their appearances without needing a measure such as applying indication members such as labels on them. Further, the use of such plunger rods makes it possible to provide syringes of significantly enhanced visual identifiability without impairing high-level quality, functions, sanitariness and safety required for the syringes.

15 Claims, 7 Drawing Sheets

(56) References Cited

FOREIGN PATENT DOCUMENTS

| JP | 2004-188199 A | 7/2004 |
|---|---|---|
| JP | 2004-208740 A | 7/2004 |
| JP | 2006-520639 A | 9/2006 |

OTHER PUBLICATIONS

Japanese Office Action for Japanese Patent Application No. 2010-500499 dated Jan. 24, 2012.

* cited by examiner

PLUNGER ROD AND SYRINGE

This application is a U.S. national phase filing under 35 U.S.C. §371 of PCT Application No. PCT/JP2008/053603, filed Feb. 29, 2008, which is hereby incorporated in its entirety by reference.

TECHNICAL FIELD

This invention relates to a plunger rod and a syringe, and more specifically, is concerned with a plunger rod for a syringe, said plunger rod being colored in part or in whole, and also with a high-identifiability syringe making use of the plunger rod.

BACKGROUND ART

An administration of a drug solution to a patient by a syringe is carried out by a procedure such as that to be described hereinafter. After the drug solution is first drawn from an ampoule or vial and filled in a syringe barrel by using a plunger rod, the plunger rod is slowly pushed into the syringe barrel so that the drug solution is injected directly or via an infusion tube into a blood vessel or the like of the patient. Syringes, which are used as described above, are substantially the same in configuration from the request for giving priority to their basic function, and even among those having syringe barrels different in thickness and/or length because of differences in capacity, they all give a similar impression in appearance so that their own visual identifiability is extremely low. Further, syringes are fundamentally used with different kinds of drug solutions filled therein, respectively, as needed depending on the symptoms of patients. Before use, syringes of the same kind cannot hence be identified from each other at all from their appearances. In general, a syringe barrel is transparent, and a drug solution filled therein is visible from the outside. The drug solution is not characterized by color either so that, even when the drug solution has been filled in the syringe barrel, the thus-filled syringe is not provided with any substantially-improved visual identifiability. In a medical procedure, on the other hand, it is essential to absolutely avoid any misidentification or confusion with respect to each drug solution to be administered to a patient. For this purpose, it is necessary to permit clearly distinguishing a drug solution filled in a syringe barrel and its intended purpose when seen from the outside.

For permitting clearly distinguishing a drug solution filled in a syringe barrel, various measures have heretofore been taken to provide the thus-filled syringe with improved visual identifiability. Examples of such measures include to directly write necessary information, such as the name of a drug solution, the name of a patient and an intended purpose, on an outer wall of a syringe or to adhere a label bearing such information written thereon. It has also been proposed to prepare beforehand an indication member, for example, a slip of paper with necessary information such as the name of a drug solution and the name of a patient written thereon and to attach it to a syringe by a rubber band or the like. In order to resolve the difficulty in reading scale markings or the like that would arise when a label or indication member is adhered or otherwise attached to a syringe barrel, it has also been proposed to show information by inserting such an indication member in place within a bore formed in a thumb rest of the syringe (see Patent Document 1).

Patent Document 1: JP-A-2003-260136

DISCLOSURE OF THE INVENTION

Problem to Be Solved by the Invention

However, none of the conventional measures are such that would enhance the visual identifiability of a syringe itself, and permit identifying a drug solution filled in a syringe barrel and obtaining information or the like on a patient, to which the filled drug solution is to be administered, by simply taking a glance. Moreover, the size of an area in an indication member such as a label, where information can be written, is limited, and even with such an indication member being arranged, the visual identifiability of a syringe can by no means be considered to be high. On the other hand, there are very numerous kinds of drug solutions. It is, therefore, not easy to fill a desired drug solution in a syringe while completely avoiding misidentification or confusion. To avoid the occurrence of misidentification or confusion with respect to a drug solution to be filled in a syringe, close attention is paid to the filling work of the drug solution in the syringe such as attaching beforehand an indication member, on which the drug solution to be filled and other information are described, to the syringe and filling the drug solution while confirming the details of the description of the indication member. Further, the filling work of syringes is often performed at once. In such filling work, a single kind of drug solution is filled in the plural syringes, or plural kinds of drug solutions are separately filled in the plural syringes. Even when each syringe is provided with an indication member, extremely careful and safe handling is required for filling a variety of drug solutions in the respective syringes, which are extremely low in visual identifiability, without completely avoiding misidentification or confusion and for administering the filled drug solutions to patients without any mistake.

With such current circumstances in view, the present inventors have arrived at contemplating that it would be very useful even for syringes of exactly the same configuration if the individual syringes themselves would be provided with enhanced visual identifiability. Described specifically, if plural syringes can be visually and individually identified although they are of the same kind and if their visual identities can be instantly recognized, the plural syringes of the same kind can be grouped depending on their characteristic features, and these characteristic features can be made corresponding to variables such as, for example, the kinds of drug solutions to be filled and the concentrations of the drug solutions. If handling is carried out relying upon this grouping, the worker is allowed to perform the handling while confirming the characteristic feature of each syringe, said characteristic feature being recognizable by simply taking a glance at the external appearance of the syringe, upon filling the syringe or upon administering its drug solution. The construction of each syringe in the above-described manner also makes it possible to more effectively avoid potential misidentification or confusion of a drug solution that would otherwise take place upon filling a syringe barrel with the drug solution or upon administering the filled drug solution.

It is to be noted that upon making improvements in a syringe, the following matter needs to be fully kept in mind from the special features of its application. Described specifically, a syringe is used in a medical procedure, and a drug solution filled in its syringe barrel is administered into the body of a patient. The safety of the syringe must, therefore, be secured absolutely. Accordingly, it is essential to absolutely avoid such a situation that the high-level quality, function, sanitariness and safety required for the syringe would be impaired even if an improvement can be made in the visual identifiability of the syringe itself.

An aspect of the present invention is, therefore, to provide a plunger rod capable of applying to a syringe a characteristic feature that makes it possible to readily and visually identify the syringe by simply taking a glance at its external appearance without using such a measure as attaching an indication member such as a label even if the syringe has exactly the same external appearance and configuration as plural other syringes. Another aspect of the present invention is to provide a syringe of significantly improved visual identifiability by using such a plunger rod without impairing the high-level quality, function, sanitariness and safety required for the syringe.

Means for Solving the Problem

The above-described aspects can be achieved by the present invention to be described hereinafter. Described specifically, the present invention provides a plunger rod for a syringe, said plunger rod being useful for sliding a piston within a syringe barrel, wherein the plunger rod is colored in part or in whole.

Preferred embodiments of the above-described plunger rod can include the followings: (1) the plunger rod comprises a cylindrical barrel body provided at a leading end thereof with a piston-supporting portion formed integrally with the barrel body and a cap fitted in a hollow opening located in the barrel body at an opposite end where the piston-supporting portion is not arranged, and at least the cap is colored; (2) the plunger rod as described above in (1), in which the cap and a portion other than the cap are colored in different colors, respectively; and (3) any one of the plunger rods described above, in which a texture pattern or drawing pattern is formed by the coloring.

In another aspect of the present invention, there is also provided a syringe composed of a syringe barrel, a piston inserted within the syringe barrel, and a plunger rod with the piston supported thereon for sliding the piston, wherein the plunger rod is one of the plunger rods described above.

Advantages Effects of the Invention

According to the present invention, it is possible to provide a plunger rod capable of applying to a syringe a characteristic feature that makes it possible to readily and visually identify the syringe by simply taking a glance at its external appearance without taking such a measure as attaching an indication member such as a label even if the syringe has exactly the same external appearance and configuration as plural other syringes. According to the present invention, it is also possible to provide a useful syringe of significantly improved visual identifiability by using the above-described plunger rod without impairing the high-level quality, function, sanitariness and safety required for the syringe. According to the preferred embodiments of the present invention, it is also possible, in addition to the above-described plunger rod and syringe, syringes capable of applying visual identifiability pursuant to desires from users.

BEST MODES FOR CARRYING OUT THE INVENTION

The present invention will hereinafter be described in detail based on preferred embodiments. Descriptions will be made with reference to drawings that illustrate examples of certain preferred embodiments of the plunger rod according to the present invention. The plunger rod according to the present invention is characterized in that it is colored in part or in whole. FIG. 1 and FIG. 2 are perspective views showing examples of the plunger rod according to the present invention, both of which are colored in whole. FIG. 3, FIG. 4 and FIG. 6 are perspective views showing other examples of the plunger rod according to the present invention, all of which are colored only in part. A description will first be made about advantageous effects available from the use of the invention plunger rod constructed as described above.

Considering that, if a syringe can be provided with enhanced visible identifiability by a simple measure without impairment to the function and safety required for the syringe, the above-described problems of the conventional syringes would be solved to provide a useful syringe which has high practical utility and enhanced convenience and which at the same time, can more effectively avoid an accident that a wrong drug solution would be administered to a patient, the present inventors have enthusiastically conducted investigations, and as a result, have led to the present invention. The present inventors first conducted an investigation on components of a syringe, that is, a syringe barrel, a piston which slides within the syringe barrel, and a plunger rod. As a result, with attention focused on the fact that among these components, the plunger rod has broader options with respect to its material compared with the other components because the plunger rod is not brought to direct contact with a drug solution, the present inventors came to a conclusion that it would be effective to make improvements in the plunger rod among the components of the syringe. As a result of a further investigation, it was found that, when plunger rods as components of plural syringes having the same configuration in external appearance are colored in part or in whole, their use would provide even the plural syringes themselves with enhanced individual visible identifiability, and moreover, their differences are extremely pronounced so that the individual syringes can be readily identified by simply taking a glance at them. A plunger rod can be formed from a synthetic resin, and therefore, it is extremely easy to color it in part or in whole. In addition, its color can be considered to be infinite. The coloring of the plunger rod can, therefore, meet any desire. Moreover, the coloring of the plunger rod in part or in whole is extremely easier as a processing step compared with modifications of its configuration, and does not significantly affect its manufacturing cost.

A syringe itself can be provided with enhanced visual identifiability when its plunger rod as a component of the syringe is colored in part or in whole and the resulting colored plunger rod is used. As a consequence, the syringe can be used as will be described hereinafter. If syringes colored in different colors at colored parts of their plunger rods, for example, for respective kinds of drug solutions to be filled in their syringe barrels, respective concentrations of a drug solution, or respective administration routes such as oral and enteral administrations are provided and the syringe-color correlations are set to always remain constant, the details of the drug solution filled in each of the syringes can be instantly ascertained by simply taking a glance on it. A medical practitioner who is about to administer the drug solution by one of the syringes can, therefore, confirm the kind or the like of the drug solution filled in its syringe barrel by simply taking a glance at the colored part of its plunger rod, said colored part characterizing the syringe, in addition to ascertaining the drug solution based on an indication member such as a label. Further, the differences in color at the colored parts of the plunger rods, said colored parts characterizing the individual syringes, can be instantly recognized even by patients themselves or by other people around the patients and medical practitioners. Therefore, a patient or any other person around the patient and medical practitioner can also become readily aware of any mistake in syringe selection in a situation such that syringes of the same color are used routinely for the patient. It, therefore, becomes possible to avoid the accident that a wrong drug solution would be administered to a patient.

In recent years, pre-filled syringes with drug solutions filled in syringe barrels thereof have also been finding widespread utility for the purpose of reducing the work load in medical care practice or for a like purpose. Adhered on an outer wall of each syringe barrel is a label, which shows information on the filled drug solution such as its name, concentration and fill volume. To enhance the mutual identifiability of syringes filled with different drug solutions, various contrivances have been made to labels to be adhered on the syringes. There is, however, a limitation on the contrivances to such label indications. Even with such a pre-filled syringe, it is, therefore, possible to avoid the accident that a wrong drug solution would be administered to a patient as in the case of the above-described syringe that is used by filling a drug solution in it, if the pre-filled syringe can be enhanced in visual identifiability by a characteristic feature applied to its syringe itself.

In addition, the provision of syringes themselves with enhanced own identifiability is also very useful, as will be mentioned below, upon filling work of a drug solution into the syringe barrel of each of the syringes. If a syringe which is different in color at a colored part of its plunger rod is provided for every kind or concentration of drug solution to be filled and further for every patient to whom the drug solution is to be administered, a person who conducts the filling work can conduct the filling work of the drug solution while confirming the correlation between the difference of the color and the difference of the kind or the like of drug solution. In the filling work into the syringe barrel, the worker can more surely conduct the filling work of the drug solution. As a consequence, it is possible to more effectively avoid the potential occurrence of misidentification or confusion that may arise at the stage of the filling work of the drug solution into the syringe barrel. Further, with a syringe that makes use of the plunger rod according to the present invention, information on the filled drug solution and the like can be obtained based on the difference of the applied color. It is, therefore, possible to attach an indication member such as a label to the syringe with the drug solution filled therein after completion of the filling work. As the drug solution filled in the syringe barrel can be identified by solely relying upon the difference of the color of the colored part of the plunger rod according to the present invention, it may be possible to omit the work itself that attaches the indication member such as the label to the syringe.

With reference to the drawings, a description will next be made about certain embodiments of the plunger rod according to the present invention. FIG. 5 is an illustration that shows a plunger rod 1 according to the present invention in its use. The plunger rod according to the present invention is used to slide a piston 11, which is arranged on a leading end of the plunger rod, within a syringe barrel 12 of a syringe 21. Its function and configuration are not specifically limited, and can be similar to those known to date. The plunger rod may have a novel configuration particularly suited for the present invention, such as that depicted in FIG. 6 which will be described subsequently herein. It is to be noted that sign "A" shown in FIG. 5 indicates a direction in which the piston 11 slides. As illustrated in FIG. 1, the plunger rod 1 according to the present invention has, like conventional plunger rods, a rod-shaped configuration that is basically provided at the leading end thereof with a piston-supporting portion 2 and at an opposite end thereof with a thumb rest 3. Similar to ordinary plunger rods, a peripheral edge of the thumb rest 3 against which the thumb is pressed upon conducting the work has a greater diameter than a peripheral edge of a rod-shaped part that connects the piston-supporting portion 2 and the thumb rest 3 with each other, and forms a flange 4. The plunger rod is configured such that the piston rod 11 is slid by the plunger rod with fingers hooked on the flange 4.

Plunger rods 1,1 shown in FIG. 1 and FIG. 2, respectively, are illustrative embodiments of the plunger rod according to the present invention, and are both colored in whole. The plunger rod 1 shown in FIG. 1 is colored in a single color in whole. On the other hand, the plunger rod 1 shown in FIG. 2 is also colored in whole, but the part of a thumb rest 3 and the remaining parts are different in color. Plunger rods 1,1 shown in FIG. 3 and FIG. 4, respectively, are other illustrative embodiments of the plunger rod according to the present invention, and are both colored in part. The plunger rod 1 shown in FIG. 3 is colored at only the part of a thumb rest 3 that forms the plunger rod 1. The plunger rod 1 shown in FIG. 4, on the other hand, is colored at parts other than the part of a thumb rest 3. The colored part in the plunger rod according to the present invention can be any part as described above. It is, however, preferred to color at least the part of the thumb rest 3, because the plunger rod is adapted to slide within the syringe barrel the piston located on the leading end of the plunger rod and the plunger rod is mostly inserted in the syringe barrel under some circumstances, but the part of the thumb rest 3 is visible from the outside under any circumstance and can always provide the syringe with enhanced identifiability. It is particularly preferred to construct the plunger rod such that the thumb rest 3 is colored at its planar part against which the thumb is pressed upon pushing the piston. The planar part is always visible from the outside, and is located on a side opposite to the side of the rod-shaped part to be inserted into the syringe barrel (see, for example, FIG. 3). In each of the shown embodiments, the colored part or parts are shown in a single color. However, each colored part may be colored in plural colors, and may also present a texture pattern or drawing pattern. Depending on the manner of selection of a color and/or a texture pattern or drawing pattern upon conducting the coloring, it is possible to indicate information on a drug solution or the like to be filled in a syringe barrel. The use of plunger rods according to the present invention in individual syringes makes it possible, relying upon the differences of colors, patterns and the like of the colored parts of the plunger rods or the positional differences of the colored parts, to instantly distinguish the individual syringes by simply taking a glance at them even if the syringes have exactly the same appearance and configuration.

As a material for forming the plunger rod according to the present invention, it is necessary to use a material which is equipped with fundamental properties required for medical instruments such as antifouling property and chemical resistance and which permits sterilization and disinfection treatment or the like. In addition, the material to be used is also required to be readily colorable. Usable examples include glass, general-purpose resins such as polyethylene and polypropylene, and hard resins such as cyclic polyolefin resins, polycarbonate resins and polystyrene resin. Among these, it is preferred to use a hard resin which enables mass production at low cost. It is also preferred to use a hard resin having heat resistance and radiation resistance, because plunger rods are subjected to sterilization treatment whenever necessary. As such a resin, radiation-resistant polypropylene, cyclic olefin resin or the like can be mentioned. The plunger rod according to the present invention can be obtained by a known processing procedure such as injection molding as has conventionally been done. No particular limitation is imposed on a method for coloring the plunger rod in part or in whole. For example, a colorant such as a pigment may be added to the above-mentioned material, and processing may then be performed using the thus-colored material. As an alternative, after the plunger rod is formed from an uncolored material, the plunger rod may be directly printed at a surface thereof by a printing machine or the like to color it. When it is desired to color the plunger rod in whole, the use of a process that mixes a colorant in a forming material is preferred. When it is desired to color the plunger rod in part, on the other hand, it is preferred to use a method that prints the plunger rod at a surface thereof, or multicolor molding. In addition, the plunger rod 1 according to the present invention is not particularly limited in size, to say nothing of configuration, and its size and configuration may be determined as needed depending on the application and intended purpose of the syringe 21 in which it is used.

The plunger rods of such a conventional configuration as shown in FIG. 1 through FIG. 4 can be integrally molded from a synthetic resin. In this case, it is easier to color the molded bodies in whole rather than to color them only at desired parts. It has been found that, if a plunger rod is formed into a novel structure composed of two members as depicted in FIG. 6 and FIG. 7, on the other hand, the plunger rod can be specifically colored only at a part thereof required to enhance the visual identifiability of the syringe and the plunger rod so colored can be used in various manners. Moreover, the plunger rod having this configuration is also excellent in the function of sliding the piston within the syringe barrel compared with the plunger rods of the conventional configurations shown in FIG. 1 through FIG. 4. Described specifically, the plunger rod according to this preferred embodiment of the present invention is characterized in that it is formed of a cylindrical barrel body and a cap as a member discrete from the barrel body and at least the cap is colored, and has a construction that the cap is fitted in a hollow opening formed in an end portion of the barrel body of the plunger rod. As a consequence, the plunger rod according to this preferred embodiment of the present invention has a construction that as illustrated in FIG. 6, the plunger rod is colored at a portion of a planar part of a thumb rest 3, said planer part being not a side on which a piston to be inserted in a syringe barrel is arranged and being always visible from the outside. A description will hereinafter be made about the plunger rod according to this embodiment of the present invention.

FIG. 6 is a perspective view depicting the plunger rod 1 according to the above-described preferred embodiment of the present invention, and FIG. 7 is an exploded perspective view of the plunger rod. As illustrated in FIG. 6 and FIG. 7, the plunger rod of this embodiment is characterized in that it is formed of two members, one being a cylindrical barrel body 5 provided at a leading end thereof with a piston-supporting portion 2 formed integrally with the barrel body, and the other being a cap 7 of a structure that the cap is fitted in a hollow opening 6 located in an end portion of the barrel body 5 on a side where the piston-supporting portion 2 is not arranged, and at least the cap 7 is colored. As will be described below, this cap 7 has the structure that it can be closely and tightly fitted in the hollow opening 6. When this cap 7 is closely fitted in the hollow opening 6, the barrel body 5 and cap 7 are integrated together as illustrated in FIG. 6 so that the plunger rod 1 is provided with the thumb rest 3 having a planar surface against which the thumb can be firmly pressed. The cap 7 which constructs the plunger rod 1 depicted in FIG. 6 has a configuration that as illustrated in FIG. 7, it is formed of a cylindrical part 8 and a disk-shaped top part formed integrally with an end portion of the cylindrical part 8. Notches 8b are formed in a part of the cylindrical part 8. The end portion of the cylindrical part 8 is on a side where the notches 8b are not formed, and is greater in outer diameter than the cylindrical part 8 (see FIG. 7 and FIGS. 9A and 9B). Therefore, the disk-shaped top part as seen from the side of the cylindrical part 8 has a configuration such that a flange 9 is formed on and along a peripheral edge of the cylindrical part 8 (see FIGS. 9A and 9B). In the above-described plunger rod 1 of this embodiment, the barrel body 5 that forms the plunger rod is not colored, and only the cap 7 is colored. Therefore, the planar surface, which is formed on the thumb rest 3 and is used as a portion against which the thumb is pressed, centrally includes a colored, large circular area as illustrated in FIG. 6. Needless to say, the present invention is not limited to the above-described embodiment, and the barrel body 5 may be colored in the same color as the cap 7 or in a color different from the cap 7 such that the plunger rod is colored in whole (see FIG. 11).

The members which make up the plunger rod 1 of the above-described embodiment, that is, the barrel body 5 and cap 7 will each be described in detail. FIG. 8A is a view of the barrel body 5, which forms the plunger rod, as seen in the direction of arrow X of FIG. 7, and FIG. 8B is a view of the barrel body 5, which forms the plunger rod, as seen in the direction of arrow Y of FIG. 7. It is to be noted that in FIG. 8B, an illustration of a part of the piston-supporting portion 2, said part being seen through a hollow section of the barrel body 5, is omitted. FIG. 9A is a view of the cap 7, which forms the plunger rod, as seen in the direction of arrow M of FIG. 7, and FIG. 9B is a view of the cap 7, which forms the plunger rod, as seen in the direction of arrow N of FIG. 7. As depicted in FIG. 7 and FIG. 8A, the cylindrical piston-supporting portion 2 in this depicted embodiment, said piston-supporting portion 2 being formed integrally with the barrel body 5 and being smaller in diameter than the barrel body 5, is formed on the leading end of the barrel body 5, and threads 2a are formed on a surface of the piston-supporting portion 2 to permit threaded engagement of the plunger rod with a piston 11 (see FIG. 5). As a cross-shaped rib is formed inside the cylindrical piston-supporting portion 2, the piston-supporting portion 2 is excellent in strength despite its hollow structure. When the piston 11 is brought into threaded engagement with the piston-supporting portion 2 and is attached there, the piston 11 can hence be firmly attached in a good state on the leading end of the plunger rod 1. Owing to the above-described piston-supporting portion 2, no unnecessary hollow part is allowed to remain inside the piston so that upon sliding the piston, deformations of the piston can be reduced. The piston can, therefore, be slid in a good state within the syringe barrel by manipulating the plunger rod 1 of the above-described embodiment.

The barrel body 5, which forms the plunger rod 1 of the above-described embodiment, has a cylindrical configuration, and its hollow section extends to the end portion opposite to the leading end where the above-described piston-supporting portion 2 is formed. The hollow opening 6 is, therefore, formed in the opposite end portion (see FIG. 7 and FIG. 8B). In the depicted embodiment, a flange 4 is formed integrally with the barrel body 5 on and along a peripheral edge of the hollow opening 6 as depicted in FIG. 7 and FIG. 8B. Upon using the syringe, the user can hence stably handle the syringe by keeping fingers hooked on the flange 4.

The cap 7, which forms the depicted plunger rod 1, has the structure that it is fitted and fixed while being maintained in close contact with a wall surface of the hollow opening 6 formed in the opposite end portion of the barrel body 5, and in combination with the flange 4 of the plunger rod 1, can form the thumb rest 3 having the planar surface against which the thumb can be firmly pressed. A description will hereinafter be made about these features.

As indicated in FIG. 7 and FIG. 8B, the diameter (c) of the hollow opening 6 is formed greater than the diameter (d) of the hollow section of the barrel body 5, so that the hollow opening 6 is provided with a step formed by the difference between these diameters. As the cap 7 is fitted and fixed while being kept in close contact with the wall of the hollow opening 6 having such a structure as described above, the outer diameter (e) of the flange 9 of the cap 7, said outer diameter (e) being indicated in FIGS. 9A and 9B, is designed to have a size substantially equal to the diameter (c) of the hollow opening 6. Further, the outer diameter (f) of the cylindrical part 8 of the cap 7 is designed to have a size substantially equal to the diameter (d) of the hollow section of the hollow body 5 (see FIG. 8B and FIG. 9A). Because the cap 7 and the hollow opening 6 of the barrel body 5 are constructed as described above, the flange 9 of the cap 7 hooks on the step of the hollow opening 6 as illustrated in FIG. 10 when the cap 7 is fitted into the hollow opening 6, and therefore, the cap 7 is allowed to remain at the predetermined position.

As depicted in FIG. 7 and FIG. 8B, a cylindrical collar 5a is also formed on an inner wall surface of the hollow section of the barrel body 5 at a position in the vicinity of the hollow opening 6. As depicted in FIG. 7 and FIG. 9A, on the other hand, a collar 8a is also arranged on the outer periphery of the cylindrical part 8 of the cap 7. These collars are designed such that, when the cap 7 is fitted in the hollow opening 6, the collars 5a, 8a are located adjacent to each other. Owing to the possession of such a structure, the collars 5a, 8a hook on each other as illustrated in FIG. 10. Therefore, the cap 7 will not easily slip out of the hollow opening 6 once the cap 7 is fitted in the hollow opening 6.

As depicted in FIG. 7 and FIG. 10, the cylindrical part 8 of the cap 7 of the depicted embodiment is provided at four locations thereof with the notches 8b (see FIG. 7 and FIG. 10). Owing to the provision of these notches 8b, the freedom of movements of the cylindrical part 8 in radial directions is enhanced to facilitate the fitting of the cylindrical part 8 of the cap 7 into the hollow opening 6. In addition, the cap 7 will also be prevented from easily slipping out of the hollow opening 6 once the cap is fitted into the hollow opening 6. In the plunger rod 1 of the depicted embodiment as formed by closely fitting the cap 7 as a discrete member into the hollow opening of the barrel body 5 owing to the possession of such a structure as described above, it is designed such that as illustrated in FIG. 6, the surface of the top part of the cap 7 and the planar surface of the one side of the flange 4 formed integrally with the barrel body 5 become flush with each other. Therefore, the thumb rest 3 is formed with a planar and wide surface, and can be readily handled when the syringe is used with the thumb pressed against the thumb rest.

The size of the plunger rod according to the above-described embodiment can be determined as desired in accordance with the configuration of the syringe barrel. If the plunger rod is designed, for example, such that the dimension of the outer diameter of the cylindrical barrel body 5, which forms the plunger rod, becomes substantially equal to the inner diameter of the syringe barrel as shown in FIG. 5, the plunger rod is allowed to slide while an entire smooth outer wall surface of the barrel body 5 is kept in contact with the entire inner wall surface of the syringe barrel when the plunger rod is inserted into the syringe barrel. The plunger rod is, therefore, allowed to slide very smoothly without rattling compared with the plunger rods of the conventional configuration illustrated in FIG. 1 to FIG. 4 and having the construction that the plunger rods slide while being kept in contact with the associated syringe barrels over a small area.

The above-described plunger rod exemplified in the drawings is a particularly preferred embodiment of the plunger rod according to the present invention, and needless to say, the present invention shall not be limited to it. For example, in the plunger rod 1 of the embodiment depicted in FIG. 6, one or more ribs may be formed in the hollow section of the barrel body 5. Further, the configuration of the piston-supporting portion 2, flange 4, barrel body 5, cap 7 or the like may obviously be changed from the above-mentioned one. With respect to the invention plunger rod formed of the two members, the forming materials for the barrel body 5 and cap 7 may be the same or different. For example, the barrel body 5 may be formed from such a hard resin as exemplified above, while the cap 7 may be formed from a soft resin, elastomer or synthetic rubber by taking into consideration a feeling to touch when pressed by the thumb.

The invention plunger rod according to the above-described embodiment formed of the two members can also be used as will be described hereinafter. In the case of the plunger rod of this embodiment, the barrel body 5 and the cap 7 are separately prepared, and the plunger rod is used with the cap 7 fitted in the hollow opening 6 formed in the barrel body 5. Because the fitting of the cap 7 is very simple as described above, its fitting work can also be conducted at the stage of use. For example, a plurality of uncolored barrel bodies 5 and a like plural number of caps 7 colored in various colors are provided. Upon use, the cap 7 of a color corresponding to the kind of a predetermined drug solution is chosen, and is then fitted in the hollow opening 6 formed in one of the barrel bodies 5 to provide the resulting plunger rod as a component for a syringe. In this manner, syringes having enhanced own visual identifiability can be obtained pursuant to the user's desire, so that a wide variety of manners can be contemplated with respect to their use. Therefore, the plunger rods provided as described above are very useful.

The syringe 21 according to the present invention is characterized in that it is formed of at least the syringe barrel 12, the piston 11 inserted within the syringe barrel 12, and the plunger 1 with the piston 11 supported thereon for sliding the piston 11, and the plunger rod 1 is the above-described plunger rod 1 according to the present invention (see FIG. 5). The syringe 21 according to the present invention may be a pre-filled syringe which is distributed with a drug solution filled therein. Namely, even in the case of a pre-filled syringe which is used with a label adhered beforehand thereon, the use of the plunger rod 1 according to the present invention makes it still easier to visually identify the syringe 21.

LEGEND

Figure 1:
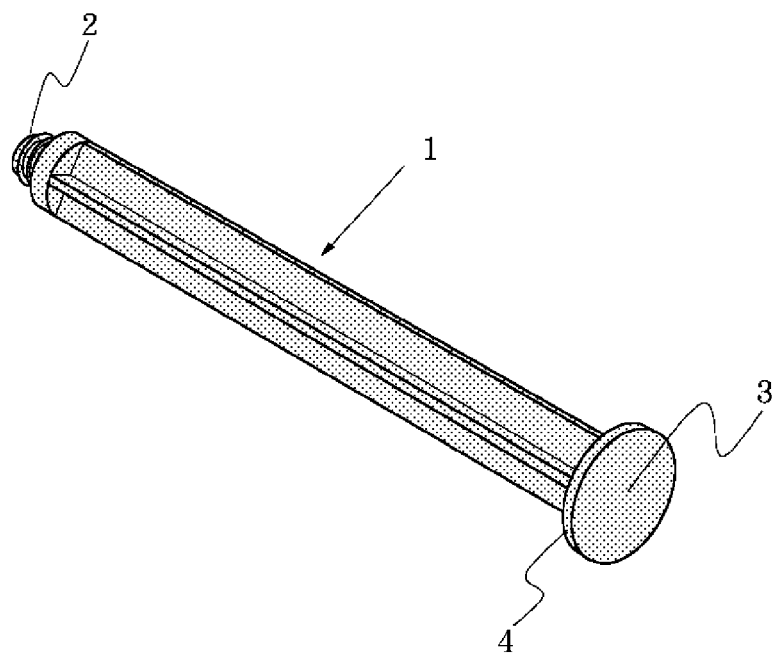
FIG. 1 is a perspective view showing an embodiment of the plunger rod according to the present invention.
Figure 2:
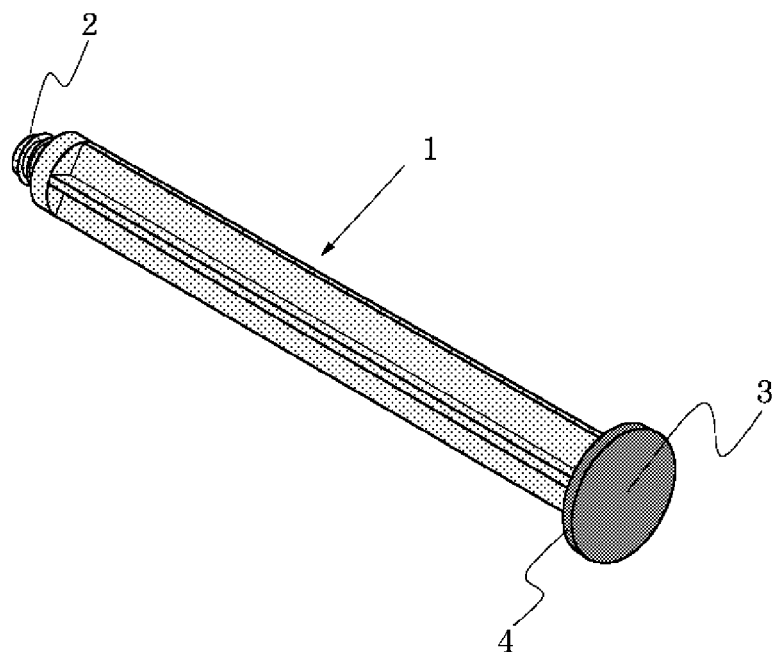
FIG. 2 is a perspective view showing another embodiment of the plunger rod according to the present invention.
Figure 3:
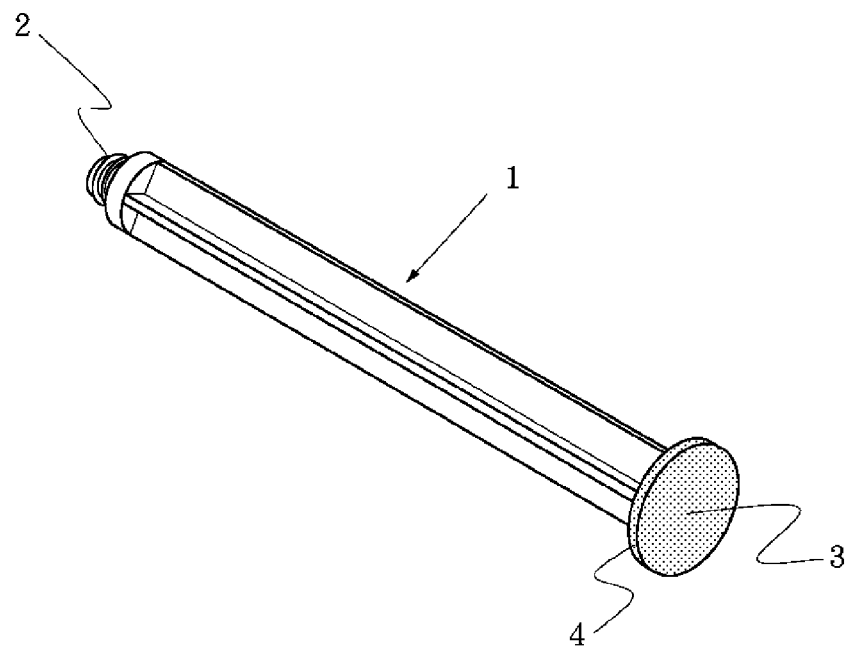
FIG. 3 is a perspective view showing a further embodiment of the plunger rod according to the present invention.
Figure 4:
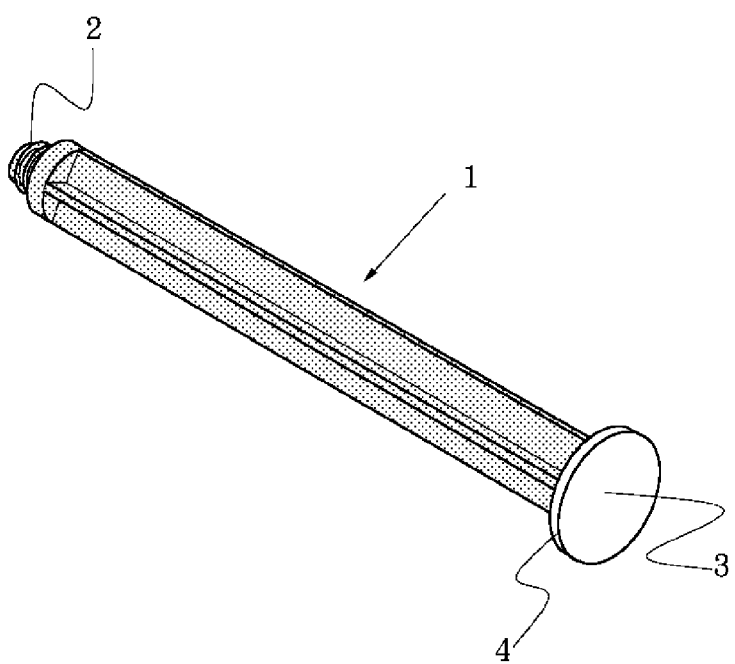
FIG. 4 is a perspective view showing a still further embodiment of the plunger rod according to the present invention.
Figure 5:
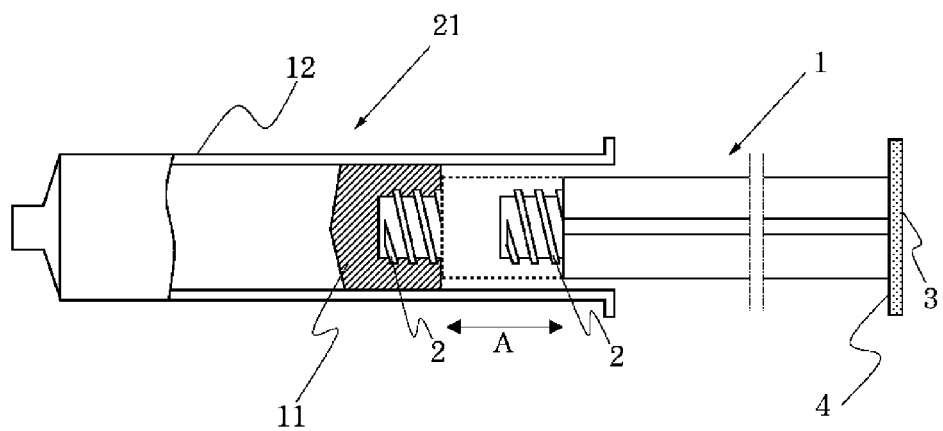
FIG. 5 is a view illustrating a manner of use of the plunger rod according to the present invention.
Figure 6:
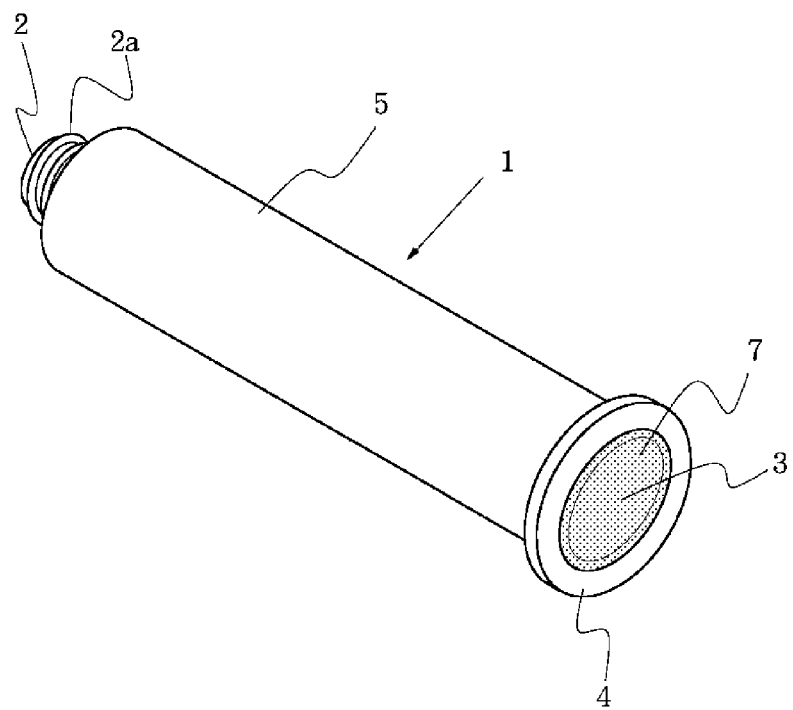
FIG. 6 is a perspective view depicting a yet further embodiment of the plunger rod according to the present invention.
Figure 7:
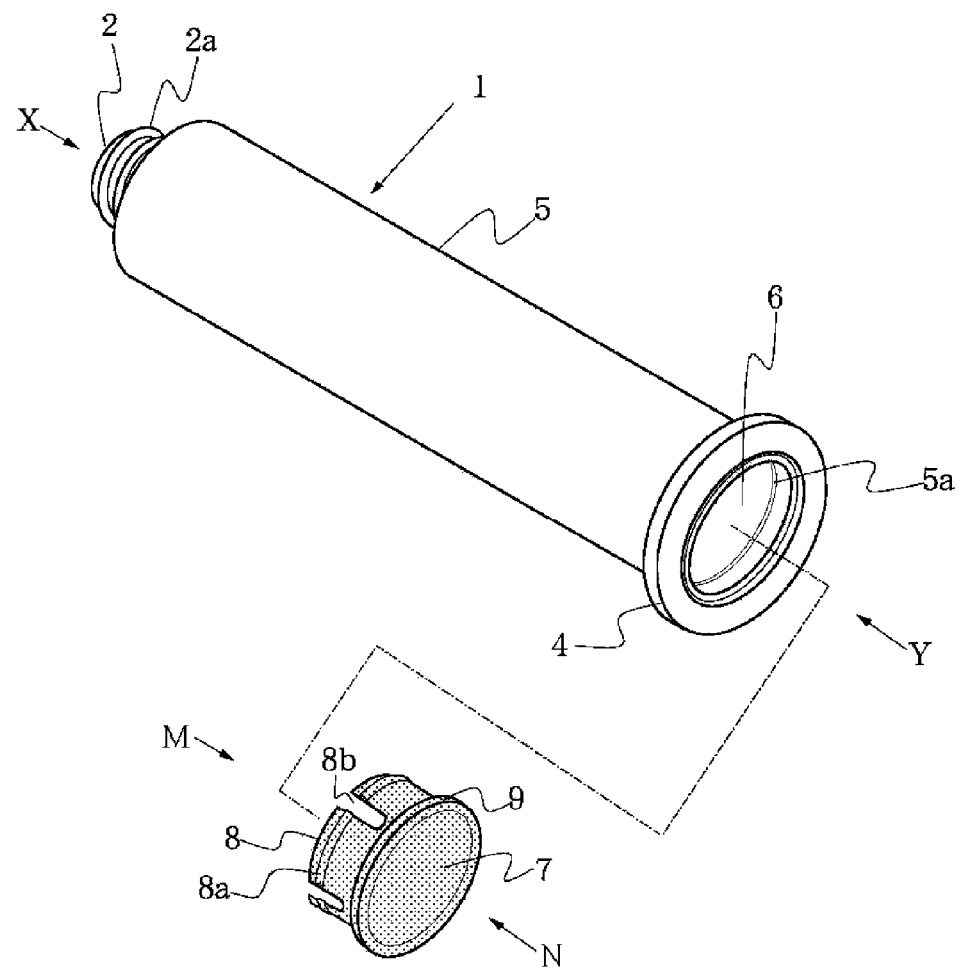
FIG. 7 is a perspective view depicting a still yet further embodiment of the plunger rod according to the present invention.
Figure 8A:
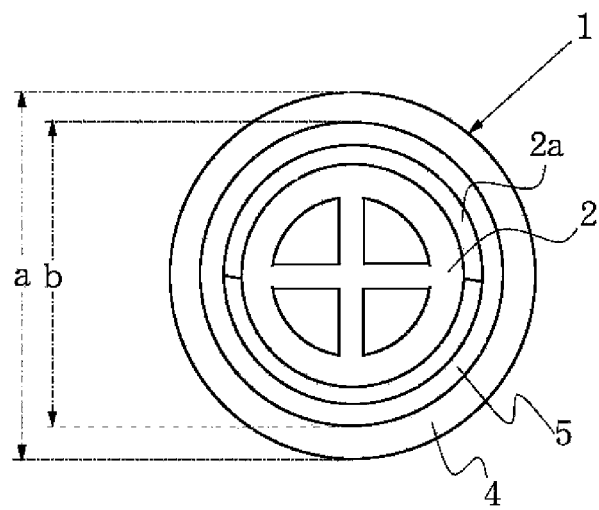
FIGS. 8A and 8B are enlarged views of the plunger rod as seen in the directions of arrows X and Y of FIG. 7, respectively.
Figure 8B:
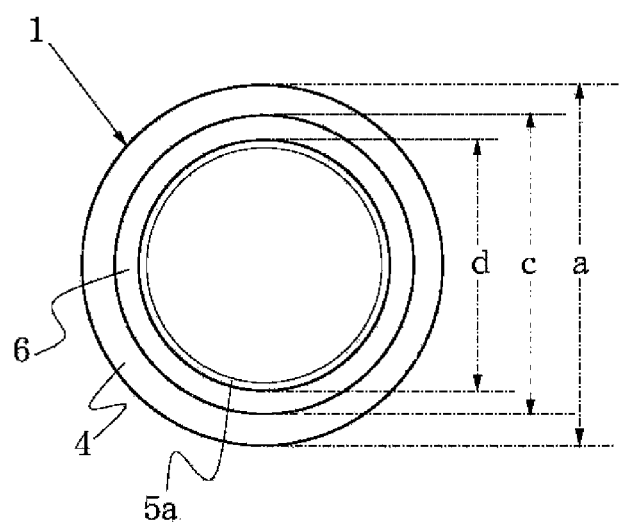
Figure 9A:
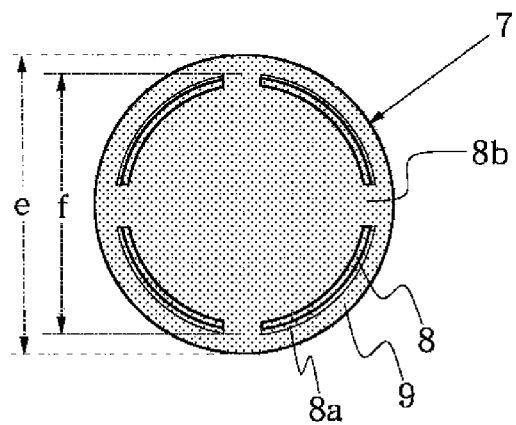
FIGS. 9A and 9B are enlarged views of the plunger rod as seen in the directions of arrows M and N of FIG. 7, respectively.
Figure 9B:
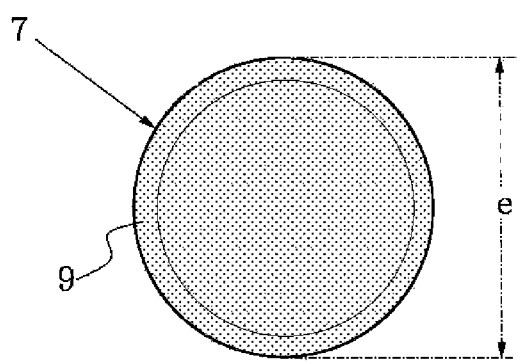
Figure 10:
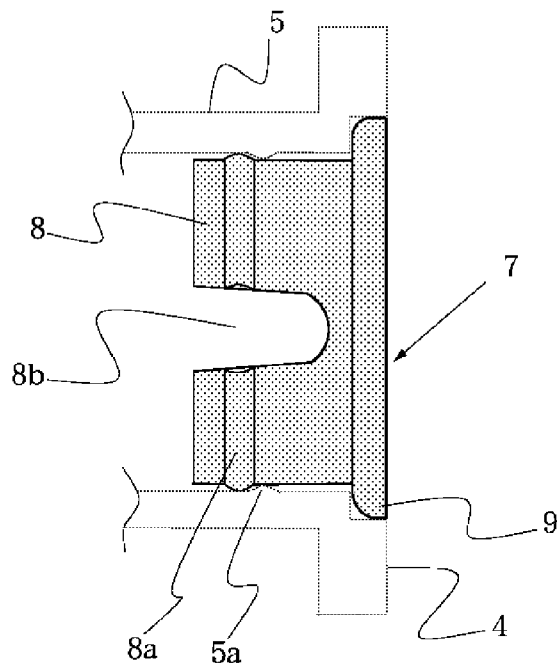
FIG. 10 is a view illustrating a state that a hollow opening is closed by a cap.
Figure 11:
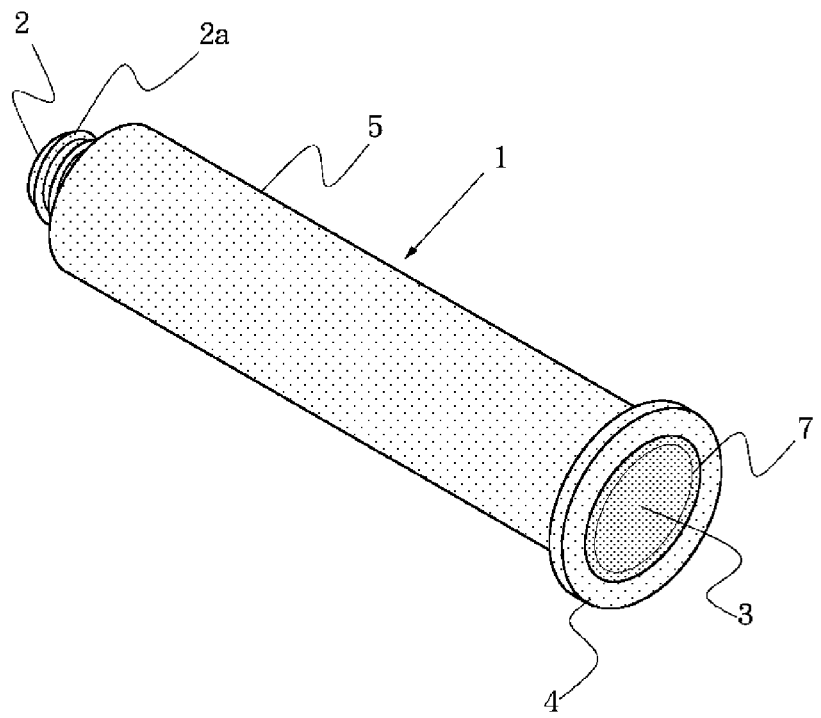
FIG. 11 is a perspective view illustrating an even yet further embodiment of the plunger rod according to the present invention.

1 Plunger rod
2 Piston-supporting portion
2a Threads
3 Thumb rest
4 Flange
5 Barrel body
5a Collar on the barrel body
6 Hollow opening
7 Cap
8 Cylindrical part
8a Collar on the cylindrical part
8b Notches
9 Flange
11 Piston
12 Syringe barrel
21 Syringe

The invention claimed is:

1. A plunger rod for a syringe, the plunger rod being configured to slide a piston within a syringe barrel, the plunger rod comprising:
 a cylindrical barrel body having a leading end, a hollow body and an opposing end, wherein the opposing end includes a hollow opening having a larger diameter than a diameter of a hollow portion of the hollow body and wherein the opposing end includes a step formed by a difference in diameter between the hollow portion of the hollow body and the hollow opening;
 a piston supporting portion formed at the leading end of the cylindrical barrel body, wherein the piston supporting portion is formed integrally with the cylindrical barrel body;
 a cap configured to be fitted in the hollow opening, the cap including a collar formed on an outer peripheral surface of the cap; and
 a cylindrical collar formed on an inner wall surface of the hollow portion of the hollow body in a vicinity of the hollow opening and that extends further inward than the entire inner wall surface;
 wherein the collar formed on the outer peripheral surface of the cap is located at a position closer to the leading end of the cylindrical barrel body than a position at which the cylindrical collar formed on the inner wall surface of the hollow portion of the hollow body is located when the cap is fitted into the hollow opening.

2. The plunger rod according to claim 1, further comprising: notches located along an outer periphery of the cap and extending in a direction substantially parallel with a central axis of the cap to allow the collar formed on the outer peripheral surface of the cap to flex inward and outward with respect to the central axis of the cap.

3. A syringe composed of a syringe barrel, a piston configured to be inserted within the syringe barrel, and a plunger rod with the piston supported thereon for sliding the piston, wherein the plunger rod is the plunger rod according to claim 2.

4. The plunger rod according to claim 1, wherein the cap and a portion other than the cap are colored in different colors, respectively.

5. The plunger rod according to claim 1, wherein the plunger rod is at least partially colored and wherein a texture pattern or a drawing pattern is formed by the coloring.

6. A syringe composed of a syringe barrel, a piston configured to be inserted within the syringe barrel, and a plunger rod with the piston supported thereon for sliding the piston, wherein the plunger rod is the plunger rod according to claim 1.

7. The plunger rod according to claim 1, wherein the cap includes a cylindrical part and a disk shaped top part, wherein the disk shaped top part is formed integrally with an end portion of the cylindrical part.

8. The plunger rod according to claim 7, wherein a plurality of notches are formed along the cylindrical part.

9. The plunger rod according to claim 7, wherein a diameter of the cylindrical part is less than a diameter of the disk shaped top part.

10. The plunger rod according to claim 7, wherein a diameter of the disk shaped top part is substantially equal to the diameter of the hollow opening.

11. The plunger rod according to claim 7, wherein a diameter of the cylindrical part is substantially equal to the diameter of the hollow portion of the hollow body.

12. The plunger rod according to claim 1, wherein the cylindrical collar formed on the inner wall surface of the hollow portion of the hollow body is formed as a continuous ring.

13. The plunger rod according to claim 1, wherein the plunger rod is at least partially colored.

14. The plunger rod according to claim 1, wherein at least the cap is colored.

15. The plunger rod according to claim 1, wherein the collar formed on the outer peripheral surface of the cap is configured to ride over the cylindrical collar formed on the inner wall surface of the hollow portion of the hollow body when the cap is fitted into the hollow opening.

* * * * *